United States Patent
Hofmeister et al.

(10) Patent No.: US 10,553,975 B2
(45) Date of Patent: Feb. 4, 2020

(54) BOARD-TO-BOARD CONNECTOR FOR SIGNAL-TRANSMITTING CONNECTION OF TWO CIRCUIT BOARDS

(71) Applicant: ROSENBERGER HOCHFREQUENZTECHNIK GMBH & CO. KG, Fridolfing (DE)

(72) Inventors: Stefan Hofmeister, Kirchanschöring (DE); Martin Räthlein, Saaldorf-Surheim (DE); Folke Michelmann, Tittmoning (DE); Markus Schichl, Seekirchen (AT)

(73) Assignee: Rosenberger Hochfrequenztechnik GmbH & Co. KG, Fridolfing (DE)

( * ) Notice: Subject to any disclaimer, the term of this patent is extended or adjusted under 35 U.S.C. 154(b) by 0 days.

(21) Appl. No.: 15/750,554

(22) PCT Filed: Jun. 14, 2016

(86) PCT No.: PCT/EP2016/000994
§ 371 (c)(1),
(2) Date: Feb. 6, 2018

(87) PCT Pub. No.: WO2017/025162
PCT Pub. Date: Feb. 16, 2017

(65) Prior Publication Data
US 2019/0013606 A1 Jan. 10, 2019

(30) Foreign Application Priority Data
Aug. 13, 2015 (DE) .................. 20 2015 005 722 U

(51) Int. Cl.
*H01R 12/00* (2006.01)
*H05K 1/00* (2006.01)
(Continued)

(52) U.S. Cl.
CPC .......... *H01R 12/732* (2013.01); *A61B 5/055* (2013.01); *H01R 12/88* (2013.01);
(Continued)

(58) Field of Classification Search
CPC ............................... H01R 13/62; H05K 3/368
USPC ........................................... 439/65, 630, 843
See application file for complete search history.

(56) References Cited

U.S. PATENT DOCUMENTS 3,482,201 A 12/1969 Schneck
5,161,981 A * 11/1992 Deak .................. H01R 12/62
439/491
(Continued)

FOREIGN PATENT DOCUMENTS

CN 1679209 A 10/2005
CN 2916965 Y 6/2007
(Continued)

*Primary Examiner* — Abdullah A Riyami
*Assistant Examiner* — Thang H Nguyen
(74) *Attorney, Agent, or Firm* — DeLio Peterson & Curcio LLC; Robert Curcio

(57) ABSTRACT

A board-to-board connector for signal-transmitting connection of a first circuit board to a second circuit board, in particular in magnetic resonance imaging scanners, wherein the board-to-board connector has a base body with a first socket for a contact section of the first printed circuit board and a second socket for a contact section of the second printed circuit board, wherein a spring element support with a plurality of spring elements is provided between the first socket and the second socket, wherein each of the spring elements makes electrical conductive contact with a contact of the respective contact sections using spring loaded contact pressure.

11 Claims, 8 Drawing Sheets

(51) Int. Cl.
    *H01R 13/187*     (2006.01)
    *H01R 24/00*     (2011.01)
    *H01R 12/73*     (2011.01)
    *A61B 5/055*     (2006.01)
    *H01R 13/24*     (2006.01)
    *H01R 13/42*     (2006.01)
    *H01R 13/50*     (2006.01)
    *H01R 12/88*     (2011.01)
    *G01R 33/28*     (2006.01)

(52) U.S. Cl.
    CPC ......... *H01R 13/2435* (2013.01); *H01R 13/42* (2013.01); *H01R 13/501* (2013.01); *G01R 33/28* (2013.01)

(56) References Cited

U.S. PATENT DOCUMENTS

| | | | | |
|---|---|---|---|---|
| 2005/0282439 A1* | 12/2005 | Nagata | ............... | H01R 13/2435 439/630 |
| 2008/0171451 A1 | 7/2008 | Shin | | |
| 2012/0190219 A1* | 7/2012 | Pai | ............... | H05K 1/142 439/65 |
| 2013/0337664 A1* | 12/2013 | An | ............... | H01R 12/79 439/65 |
| 2014/0024229 A1* | 1/2014 | An | ............... | H01R 12/79 439/65 |
| 2014/0154892 A1* | 6/2014 | Zantout | ............... | H01R 12/732 439/65 |
| 2014/0170866 A1* | 6/2014 | Wright | ............... | H05K 3/368 439/65 |
| 2016/0064839 A1* | 3/2016 | Goodman | ............... | H01R 12/91 439/65 |

FOREIGN PATENT DOCUMENTS

| | | | | |
|---|---|---|---|---|
| CN | 202434735 U | | 9/2012 | |
| EP | 1536524 A1 | | 6/2005 | |
| JP | S61-13477 U | | 1/1986 | |
| JP | 2001068184 | * | 3/2001 | ............. H01R 31/06 |
| JP | 2001068184 A | | 3/2001 | |
| JP | 2006260803 A | | 9/2006 | |

* cited by examiner

BOARD-TO-BOARD CONNECTOR FOR SIGNAL-TRANSMITTING CONNECTION OF TWO CIRCUIT BOARDS

BACKGROUND OF THE INVENTION

1. Field of the Invention

The invention relates to a board-to-board connector for the signal-transmitting connection with one another of two printed circuit boards, in particular of a magnetic resonance imaging scanner.

2. Description of Related Art

Board-to-board connectors (BTB connectors) are used to connect two printed circuit boards (PCBs) with one another in such a way that the electronic components on the two printed circuit boards can communicate with one another through the exchange of electrical signals.

For the signal-transmitting connection of two printed circuit boards with one another it is known to connect one connecting part such as a contact pin with a mating part such as a socket by plugging, whereby for example the socket is soldered onto one of the printed circuit boards. However, soldering such a mating part is laborious. The contact pin can be damaged during the plugging operation so that it is irreparably deformed and it is no longer possible to form a plugged connection. This results in a technical failure of the affected printed circuit board. Moreover, printed circuit boards are connected with one another without additional mechanical retention. Shocks and vibrations can therefore lead to an interruption of the electrical contact or contacts.

EP 1 536 524 A1 discloses a board-to-board connector with spring elements for connecting two printed circuit boards electrically. The printed circuit boards can be plugged into the housing of the board-to-board connector.

US 2008/0171451 A1 describes a board-to-board connector for connecting printed circuit boards arranged in the same plane.

JP 2001 068184 A also discloses a board-to-board connector for connecting printed circuit boards arranged in the same plane.

U.S. Pat. No. 5,161,981 A describes a press connector or high pressure connector in which flexible cables carrying conductive traces are pressed against a resilient insulator core from opposite sides, wherein the resilient insulator core is surrounded by a thin film containing conductive traces.

SUMMARY OF THE INVENTION

The invention is therefore based on the problem of devising a way of simplifying the signal-transmitting connection of two printed circuit boards and at the same time making it less susceptible to faults.

According to the invention this problem is solved through a board-to-board connector of the aforementioned kind with the features named in the independent claims. Advantageous variants of the invention are described in the further claims.

The above and other objects, which will be apparent to those skilled in the art, are achieved in the present invention which is directed to a board-to-board connector for the signal-transmitting connection of a first printed circuit board with a second printed circuit board, wherein the board-to-board connector has a main body with a first socket for a contact section of the first printed circuit board and a second socket for a contact section of the second printed circuit board, wherein a spring element support with a plurality of spring elements is provided between the first socket and the second socket, wherein each of the spring elements makes electrically conductive contact with a contact of the respective contact sections under spring-loaded contact pressure, such that the second socket is assigned a pivotable cover articulated to the main body which can be moved between an open and a closed position, wherein the second socket is formed by a guide molded onto the cover, and that the first socket is assigned to the spring element support, wherein the first socket is formed by a guide molded onto the spring element support. The board-to-board connector may be made of nonmagnetic materials.

The first socket is designed so as to predetermine a first insertion direction (I) for the contact section of the first printed circuit board, the second socket being designed so as to predetermine a second insertion direction (II) for the contact section of the second printed circuit board, wherein the first insertion direction (I) and the second insertion direction (II) are different from one another.

The first socket and the second socket are in each case designed in the form of a plug-in slot.

The board-to-board connector has at least one pin which is designed such that a cover of the main body can only be moved from its open position into its closed position if the contact sections are inserted correctly into the first socket and/or second socket. The at least one pin may be molded onto the cover.

A return spring element may be assigned to the first socket and/or the second socket.

In a second aspect, the present invention is directed to an assembly of a magnetic resonance imaging scanner, comprising a first printed circuit board and a second printed circuit board which are connected with one another in a signal-transmitting manner by means of a board-to-board connector, the board-to-board connector including a first printed circuit board with a second printed circuit board, wherein the board-to-board connector has a main body with a first socket for a contact section of the first printed circuit board and a second socket for a contact section of the second printed circuit board, wherein a spring element support with a plurality of spring elements is provided between the first socket and the second socket, wherein each of the spring elements makes electrically conductive contact with a contact of the respective contact sections under spring-loaded contact pressure, such that the second socket is assigned a pivotable cover articulated to the main body which can be moved between an open and a closed position, wherein the second socket is formed by a guide molded onto the cover, and that the first socket is assigned to the spring element support, wherein the first socket is formed by a guide molded onto the spring element support.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

DESCRIPTION OF THE EMBODIMENT(S)

Figure 1:
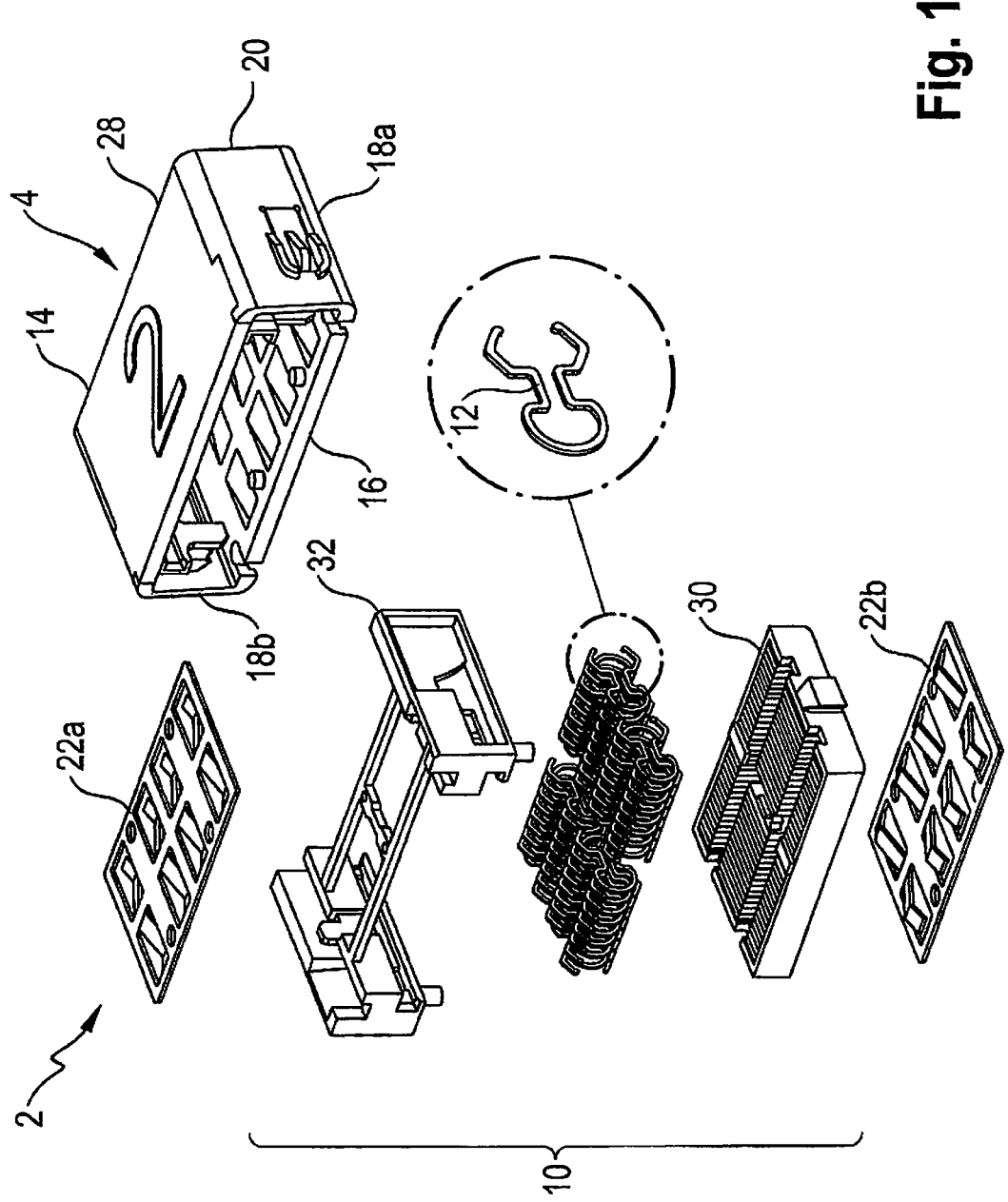
FIG. 1 shows an exploded view of an exemplary embodiment of a board-to-board connector according to the invention.

In describing the embodiment of the present invention, reference will be made herein to FIGS. 1-8 of the drawings in which like numerals refer to like features of the invention.

The board-to-board connector for the signal-transmitting connection of a first printed circuit board with a second printed circuit board according to the invention has a main body with a first socket for a contact section of the first printed circuit board and a second socket for a contact section of the second printed circuit board, wherein a spring element support with a plurality of spring elements is provided between the first socket and the second socket, wherein each of the spring elements makes electrically conductive contact with a contact of the respective contact sections under spring-loaded contact pressure.

This has the advantage that, on the one hand, no complicated soldered connection needs to be created, which reduces the cost of manufacture, and on the other hand, due to the spring contact pressure sensitive pins can be dispensed with in forming a plugged connection. Thus, the cost of manufacture is reduced and at the same time the manufacturing process is less susceptible to faults. Furthermore, it is possible to connect the two printed circuit boards by plugging without the application of force and without friction, which increases the service life of the surfaces of the printed circuit boards. Moreover, the mechanical fixing prevents damage to the contact surfaces of the contacts of the two printed circuit boards during the plugging operation, whereby, due to the mechanical fixing, the assembly consisting of the two printed circuit boards and the board-to-board connector is also less susceptible to shocks and vibrations. Finally, with the board-to-board connector a tool-free connection of two printed circuit boards with one another is possible.

According to one embodiment, the first socket is designed so as to predetermine a first insertion direction for the contact section of the first printed circuit board and the second socket is designed so as to predetermine a second insertion direction for the contact section of the second printed circuit board, wherein the first insertion direction and the second insertion direction are different from one another. For example, the first insertion direction and the second insertion direction can be virtually opposite one another. In this way, a particularly simple-to-handle board-to-board connector is provided.

According to a further embodiment, the first socket and the second socket are in each case designed in the form of a plug-in slot. In this way, the board-to-board connector can be particularly simple and at the same time particularly simple to install, which further simplifies manufacture.

The first socket is assigned to the spring element support. The first socket is also formed by a guide molded onto the spring element support. This simplifies the manufacture of the components, since the first socket and the second socket are in each case assigned different components.

The second socket is assigned a pivotable cover articulated to the main body which can be moved between an open and a closed position. The second socket is also formed by a guide molded onto the cover. The articulated cover can for example be fixed to the main body by means of a film hinge. It is thus undetachably connected with the main body.

According to a further embodiment, the board-to-board connector has at least one pin which is designed such that a cover of the main body can only be moved from its open position into its closed position if the contact sections are inserted correctly into the first socket and/or second socket. This reliably prevents errors during installation in which, due to incorrect positioning of the first and/or second printed circuit board in the first or second socket, the contacts of the contact section fail to make electrical contact with the respective spring element.

According to a further embodiment, the main body has at least one pin which is molded onto the cover. This makes it possible to use a main body which is particularly simple to manufacture.

According to a further embodiment, a return spring element is assigned to the first socket and/or the second socket. The respective return spring element is arranged opposite the spring element support, wherein in each case a gap between the spring element support and the respective return spring element defines the first or second socket. As a result of the return spring element, the contact pressure and thus the connection quality of the electrical contacts is increased.

According to a further embodiment, the board-to-board connector is made of non-magnetic materials. "Non-magnetic materials" is understood to mean materials with a relative permeability $\mu_r$ of approximately 1. These can for example be paramagnetic or diamagnetic materials. This makes it possible to use the board-to-board connector in an environment with strong magnetic fields, for example in a magnetic resonance imaging scanner.

The invention also includes an assembly comprising a first printed circuit board and a second printed circuit board which are connected with one another in a signal-transmitting manner by means of such a board-to-board connector. The assembly can also possess frames which, as protective frames of the printed circuit boards, protect edges and/or corners of the printed circuit boards against damage.

The invention is explained in more detail in the following with reference to the drawings.

Reference will first be made to FIG. 1.

The board-to-board connector 2 shown in FIG. 1 is designed for the electrically conductive connection of a first printed circuit board with a second printed circuit board in order to connect contacts of a contact section of the first printed circuit board with contacts of a contact section of the second printed circuit board in an electrically conductive manner, so that the first printed circuit board and the second printed circuit board form an assembly together with the board-to-board connector 2.

The assembly can be a component of a magnetic resonance imaging scanner (MRI scanner), wherein one of the two printed circuit boards is for example designed to control an adjustable patient table and the other printed circuit board is designed to actuate a tube body. One or both printed circuit boards can possess a frame which serves as a protective frame in order in particular to protect edges or corners of the printed circuit boards against damage.

In this exemplary embodiment, the board-to-board connector 2 comprises a main body 4, a spring element support 10 and two return spring elements 22a, 22b.

In this exemplary embodiment, the main body 4 is an injection-molded plastic part, formed as a single part, with a substantially cuboid basic form. The main body 4 has a cover 14, a base 16, two side walls 18a, 18b and a rear wall 20.

The cover 14 is fixed undetachably to the main body 4 via a pivot joint 28 designed in the form of a film hinge which can be moved between an open position and a closed position.

A spring element support 10 is provided for arrangement in the interior of the main body 4. In this exemplary embodiment, the spring element support 10 comprises a base body 30, a plurality of spring elements 12 and a securing element 32. In this exemplary embodiment, the base body 30 and the securing element 32 are injection-molded plastic parts, formed as a single part, whereas the spring elements 12 are gold components or components made of a gold-containing alloy.

Also, a return spring element 22a, 22b is in each case provided for attachment to an inner side of the cover 14 and to an inner side of the base 16. In this exemplary embodiment, the return spring elements 22a, 22b are in each case designed in the form of hold-down plates. In this exemplary embodiment, the return spring elements 22a, 22b in each case consist of a stamped and bent or angled metal sheet with a plurality of spring tongues.

In this exemplary embodiment, the board-to-board connector 2 with its components main body 4, spring element support 10 (with the base body 30 and the securing element 32 as well as the plurality of spring elements 12) and the return spring elements 22a, 22b are in each case made of a non-magnetic, for example paramagnetic and/or diamagnetic material with a relative permeability $\mu_r$ of approximately 1.

Figure 2:
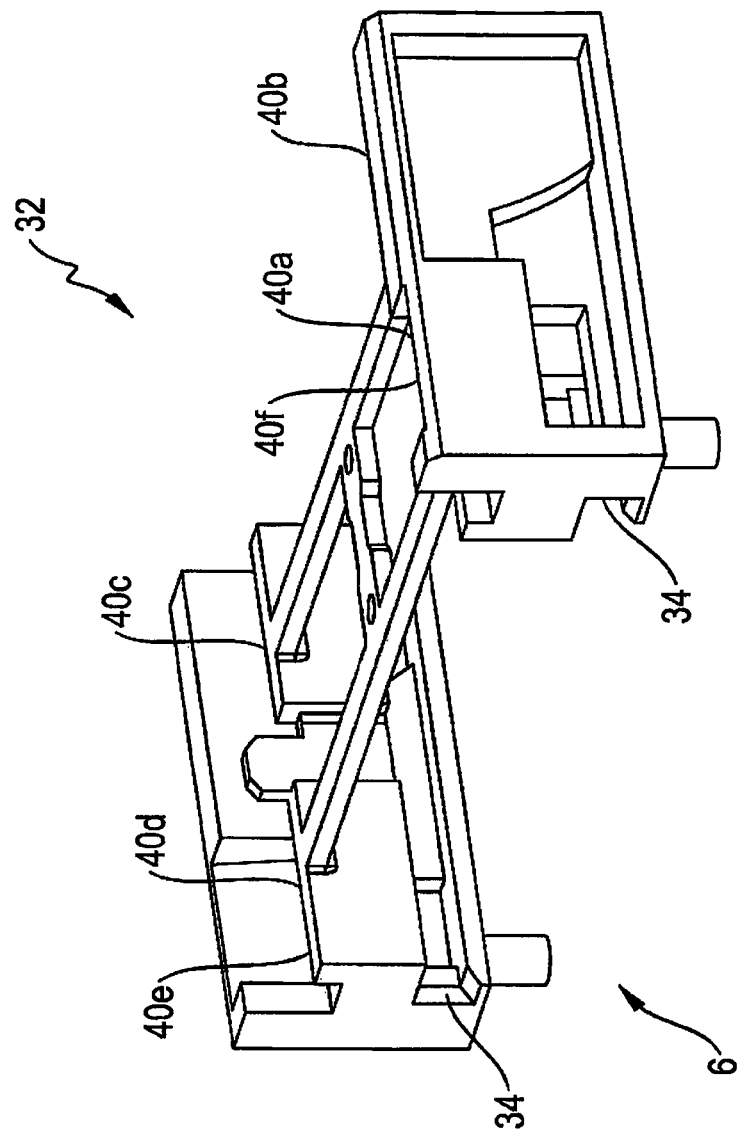
FIG. 2 shows a schematic representation of a securing element of the board-to-board connector shown in FIG. 1.

Reference will now be made, in addition, to FIG. 2.

FIG. 2 shows the securing element 32 of the spring element support 10.

Molded onto the securing element 32 is a first guide 34 consisting of two opposing guide rails. The first guide 34 defines a first socket 6 for a contact section of the first printed circuit board. A contact section of a printed circuit board is understood here to mean the section of the printed circuit board in which contacts are arranged which are to be connected in an electrically conductive manner with the spring elements 12, while various different electronic components are arranged on other sections of the printed circuit board.

Figure 3:
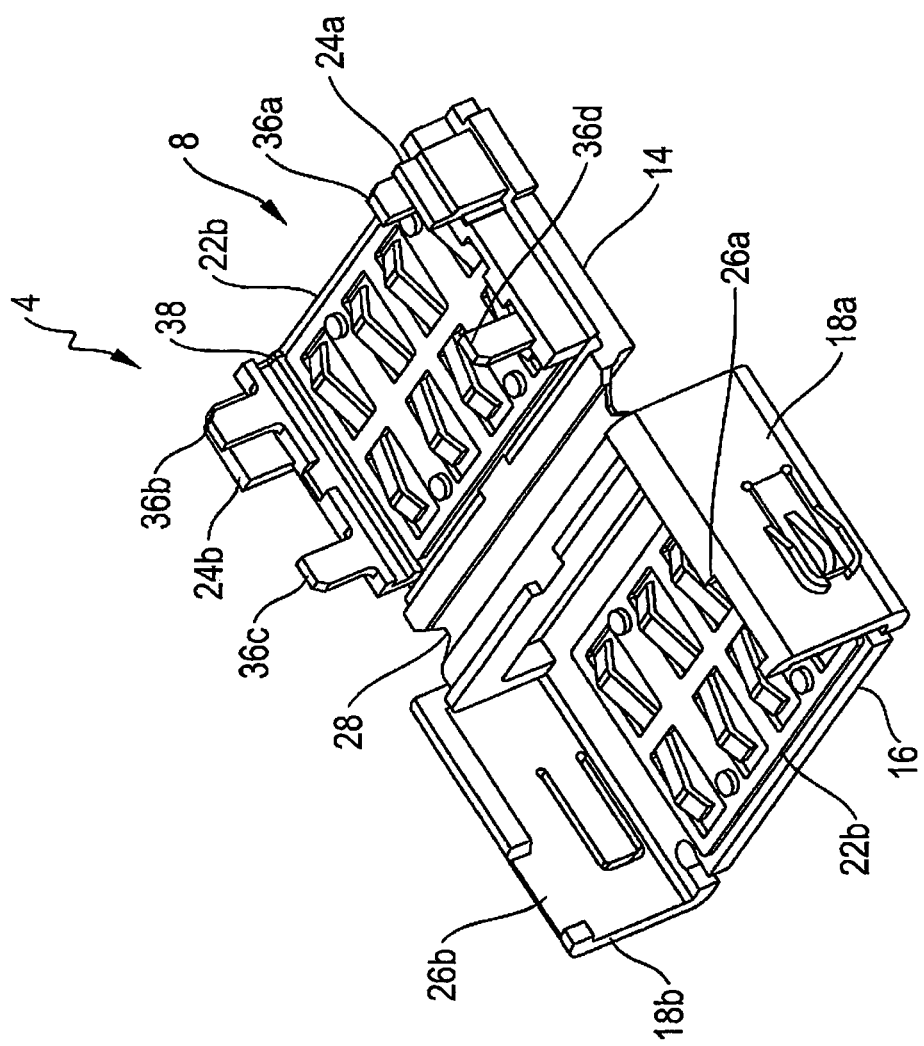
FIG. 3 shows a schematic representation of a main body of the board-to-board connector shown in FIG. 1.
Figure 4:
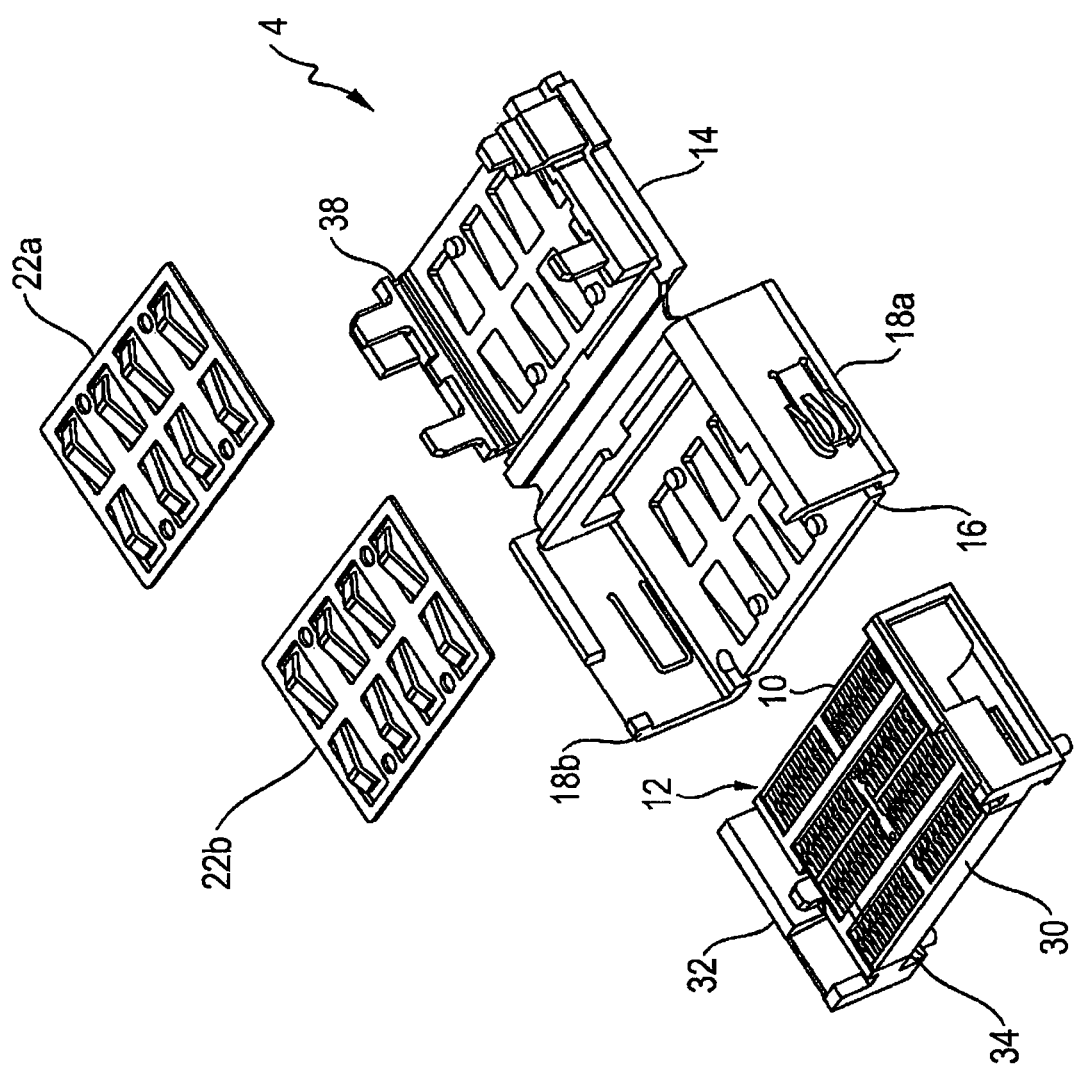
FIG. 4 shows a schematic representation of a first step in the installation of the board-to-board connector shown in FIG. 1.
Figure 5:
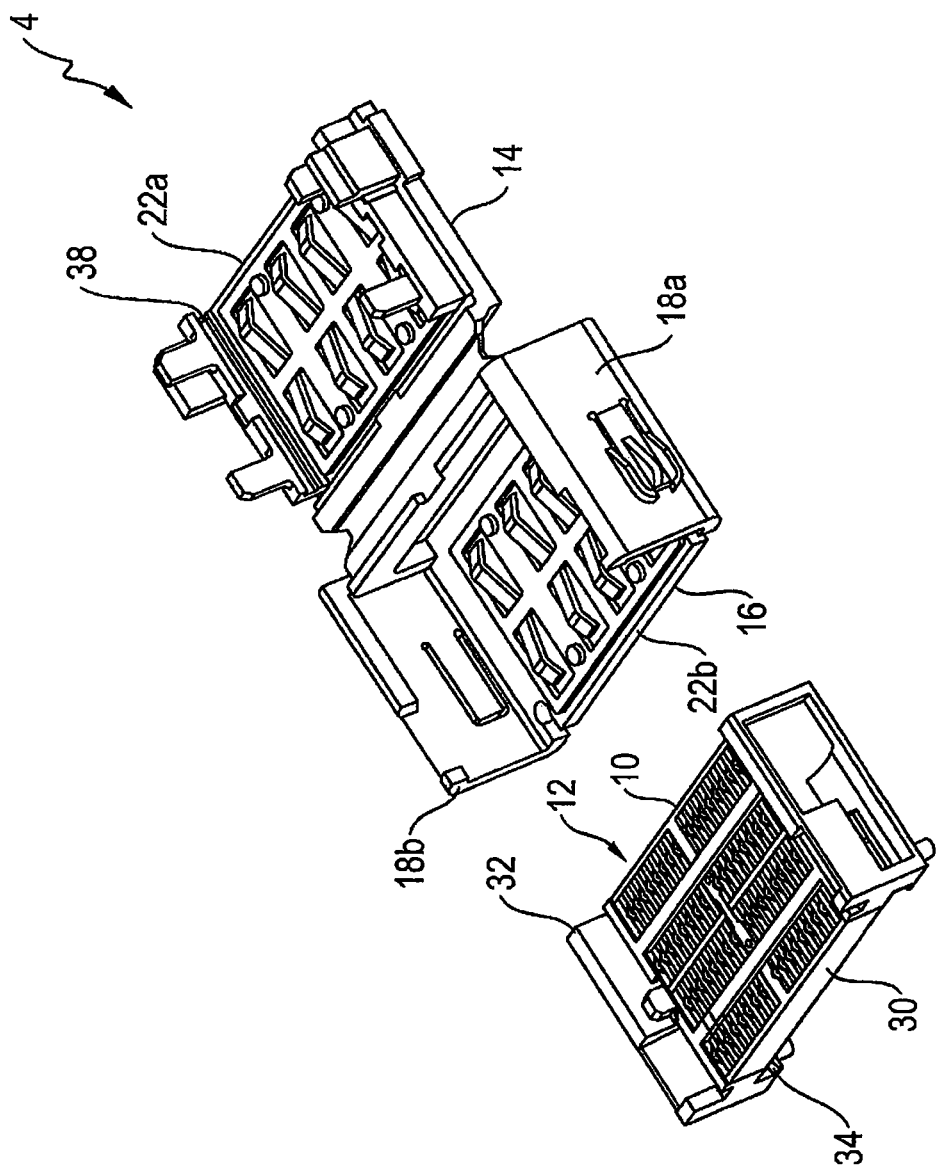
FIG. 5 shows a schematic representation of a second step in the installation of the board-to-board connector shown in FIG. 1.
Figure 6:
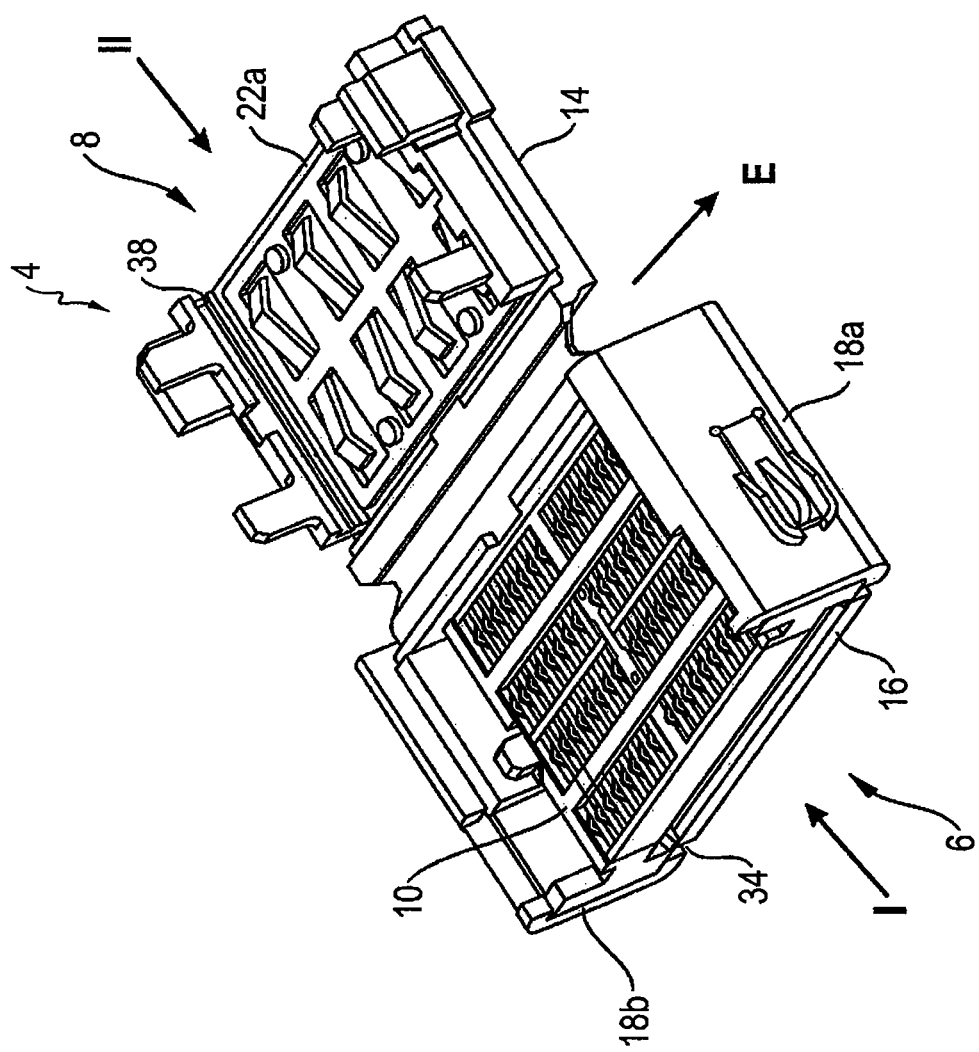
FIG. 6 shows a schematic representation of a third step in the installation of the board-to-board connector shown in FIG. 1.

Reference will now be made, in addition, to FIG. 3.

FIG. 3 shows the main body 4 with the cover 14 in its opened position. The return spring elements 22a, 22b are thereby already fixed onto the inner side of the cover 14 and onto the inner side of the base 16.

In this exemplary embodiment, in order to fix the cover 14 in its closed position, snap-in hooks 24a, 24b are molded onto the cover 14 which in the closed position can be brought into engagement with corresponding recesses 26a, 26b in the main body 4 in order to fix the cover 14 in the closed position.

A second guide 38 consisting of two opposing guide rails is also molded onto the cover 14. The second guide 38 defines a second socket 8 for a contact section of the second printed circuit board.

Also molded onto the cover 14 are pins 36a, 36b, 36c, 36d which are designed in the form of coding pins, while the securing element 32 (see FIG. 2) is provided with pin sockets 40a, 40b, 40c, 40d, 40e, 40f for receiving the pins 36a, 36b, 36c, 36d and the snap-in hooks 24a, 24b of the cover 14, in which the pins 36a, 36b, 36c, 36d and snap-in hooks 24a, 24b engage when the spring element support 10 with the securing element 32 is fitted in the main body 4 and the cover 14 is in its closed position.

In this exemplary embodiment, the main body 4 with the cover 14, the base 16, the two side walls 18a, 18b, the rear wall 20, the first guide 34 and the pins 36a, 36b, 36c, 36d is an injection-molded plastic part manufactured as a single piece.

The installation of the board-to-board connector 2 will now be explained with additional reference to FIGS. 4 to 7.

The spring element support 10 has already been pre-mounted in that the spring elements 12 are fitted into sockets for the spring elements 12 and then the spring element support 10 is connected with the securing element 32. The securing element 32 is designed such that it closes insertion openings provided for insertion of the spring elements 12 into the sockets, so that the spring elements 12 are secured in the sockets. The spring elements 12 are thereby mounted in the sockets in a floating manner.

In a first step (see FIG. 4), with the cover 14 opened, the two return spring elements 22a, 22b are fixed to the inner side of the cover 14 and to the inner side of the base 16, in this exemplary embodiment through staking.

In a second step (see FIG. 5), again with the cover 14 opened, the pre-mounted spring element support 10 is connected with the main body 4 in that the spring element support 10 is inserted between the side walls 18a, 18b and in this exemplary embodiment fixed through staking.

In a third step (see FIG. 6), a contact section of the first printed circuit board is introduced into the first socket 6 through an insertion movement along the first insertion direction I and a contact section of the second printed circuit board is introduced into the second socket 8 through an insertion movement along the second insertion direction II. In this exemplary embodiment, in a first partial step the contact section of the first printed circuit board is introduced into the first socket 6 through an insertion movement along the first insertion direction I and then, in a second partial step, the contact section of the second printed circuit board is introduced into the second socket 8 through an insertion movement along the second insertion direction II.

In this exemplary embodiment, the first insertion direction I and the second insertion direction II in each case involve insertion from the side. The first socket 6 and the second socket 8 are designed in the form of plug-in slots formed at a distance from one another.

The first insertion direction I and the second insertion direction II are thus different from one another. In this exemplary embodiment, the first insertion direction I and the second insertion direction II run opposite to one another. Also, in this exemplary embodiment the first insertion direction I and the second insertion direction II extend at an angle of substantially 90° to a direction of extension E of the pivot axis of the pivot joints 28. "Substantially" is understood here to mean within manufacturing tolerances.

In a fourth step (see FIG. 7), the cover 14 with the spring element support 10 is brought from its open position into its closed position. The pins 36a, 36b, 36c, 36d and the snap-in hooks 24a, 24b of the cover 14 thereby engage in the corresponding pin sockets 40a, 40b, 40c, 40d, 40e, 40f of the spring element support 10.

Figure 7:
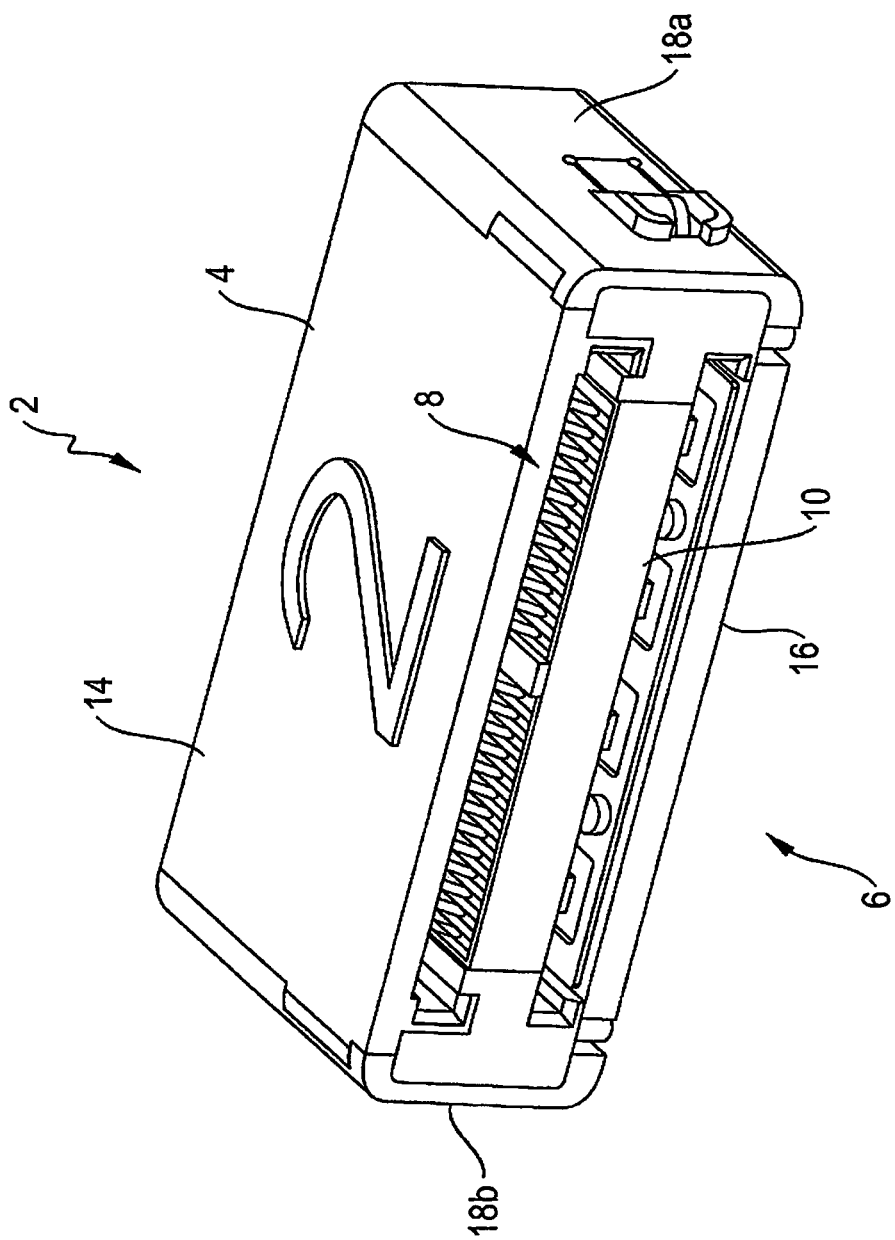
FIG. 7 shows a schematic representation of the board-to-board connector shown in FIG. 1 with closed cover.

FIG. 7 also shows that a gap is in each case formed between the spring element support 10 and the return spring elements 22a, 22b which defines the first socket 6 provided to receive the contact section of the first printed circuit board and the second socket 8 provided to receive the contact section of the second printed circuit board.

Figure 8:
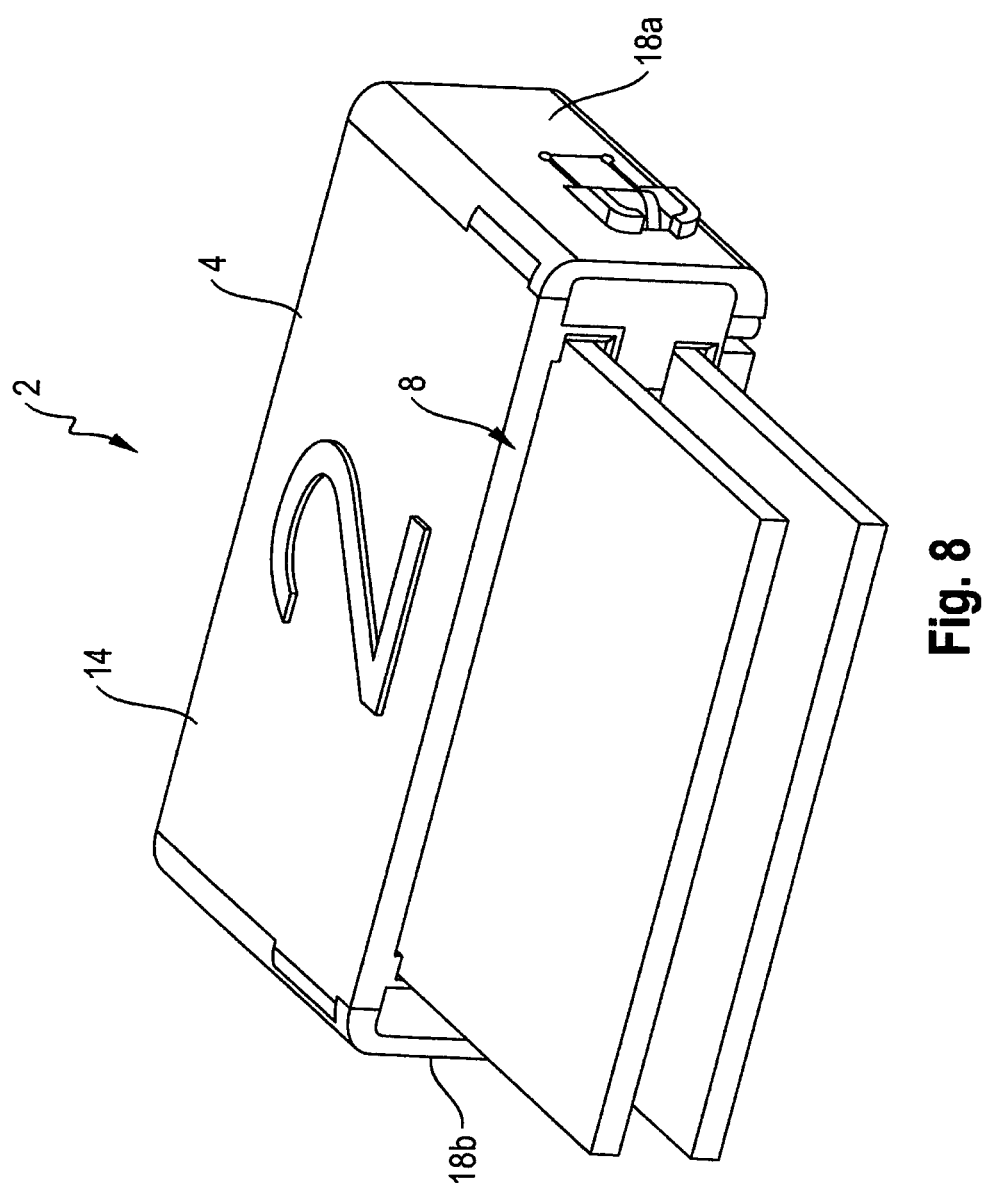
FIG. 8 shows a schematic representation of the board-to-board connector shown in FIG. 1 with closed cover, and inserted printed circuit boards.

FIG. 8 shows a schematic representation of the board-to-board connector shown in FIG. 1 with closed cover, and inserted printed circuit boards.

The pins 36a, 36b, 36c, 36d and the snap-in hooks 24a, 24b of the cover 14 are thereby designed such that it is only possible to close the cover 14 and for the snap-in hooks 24a, 24b to snap into engagement if the first printed circuit board has been inserted correctly into the first socket 6 and the second printed circuit board has been inserted correctly into the second socket 8, since in this exemplary embodiment this causes a deflection of the pins 36a, 36b, 36c, 36d and the snap-in hooks 24a, 24b.

Contact sections of the first printed circuit board are now pressed against the spring elements 12 of the spring element support 10 by the return spring element 22a, so that a secure, electrically conductive contact between the contacts of the contact section of the first printed circuit board and the respective spring elements 12 is guaranteed.

At the same time, contact sections of the second printed circuit board are pressed against the spring elements 12 of the spring element support 10 by the return spring element 22b, so that a secure, electrically conductive contact between the contacts of the contact section of the second printed circuit board and the respective spring elements 12 is guaranteed. In this way, the respective contacts of the contact sections are connected in an electrically conductive manner through the corresponding spring elements 12.

In departure from the exemplary embodiment for the installation of the board-to-board connector 2 explained with reference to FIGS. 4 to 7, the sequence of the steps can also vary, for example the sequence of the first step and of the second step can be reversed.

However, in this exemplary embodiment the first printed circuit board is only inserted into the first socket 6 when the cover 14 is opened. Otherwise the pins 36a, 36b, 36c, 36d obstruct the insertion path into the first socket 6. Thus, in this exemplary embodiment the first printed circuit board needs to be plugged in or inserted first, i.e., before the second printed circuit board. This prevents insertion in the reverse plugging sequence, i.e. first plugging the second printed circuit board into the second socket and then plugging the first printed circuit board into the first socket.

Thus, using the board-to-board connector 2, two printed circuit boards can be connected with one another in a signal-transmitting manner without creating a soldered connection, avoiding damage to sensitive pins.

LIST OF REFERENCE SYMBOLS 2 board-to-board connector
4 main body
6 first socket
8 second socket
10 spring element support
12 spring element
14 cover
16 base
18a side wall
18b side wall
20 rear wall
22a return spring element
22b return spring element
24a snap-in hook
24b snap-in hook
26a depression
26b depression
28 pivot joint
30 base body
32 securing element
34 first guide
36a pin
36b pin
36c pin
36d pin
38 second guide
40a pin socket
40b pin socket
40c pin socket
40d pin socket
40e pin socket
40f pin socket
E direction of extension
I first insertion direction
II second insertion direction While the present invention has been particularly described, in conjunction with one or more specific embodiments, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A board-to-board connector for the signal-transmitting connection of a first printed circuit board with a second printed circuit board, wherein the board-to-board connector comprises:
 a main body with a first socket for a contact section of the first printed circuit board and a second socket for a contact section of the second printed circuit board; and
 a spring element support with a plurality of spring elements provided between the first socket and the second socket, wherein each of the spring elements makes electrically conductive contact with a contact of the respective contact sections under spring-loaded contact pressure, such that the second socket is formed in part by a pivotable cover attached to the main body which can be moved between an open and a closed position, such that the second socket is formed by a guide molded onto the pivotable cover, and that the first socket is formed in part by the spring element support, such that the first socket is formed by a guide molded onto the spring element support.

2. The board-to-board connector of claim 1, wherein in the open position of the pivotable cover the first socket is designed so as to predetermine a first insertion direction (I) for the contact section of the first printed circuit board, the second socket being designed so as to predetermine a second insertion direction (II) for the contact section of the second printed circuit board, wherein the first insertion direction (I) and the second insertion direction (II) are different from one another.

3. The board-to-board connector of claim 1, wherein the first socket and the second socket are in each case designed in the form of a plug-in slot.

4. The board-to-board connector of claim 1, wherein the board-to-board connector has at least one pin which is designed such that the pivotable cover of the main body can only be moved from its open position into its closed position if the contact sections are inserted correctly into the first socket and/or second socket.

5. The board-to-board connector of claim 4, wherein the at least one pin is molded onto the cover.

6. The board-to-board connector of claim 5, wherein gaps are formed between the spring element support and return spring elements which define the first and second socket.

7. The board-to-board connector of claim 1, wherein a return spring element is attached to the first socket and/or the second socket.

8. The board-to-board connector of claim 1, wherein the board-to-board connector is made of nonmagnetic materials.

9. The board-to-board connector of claim 1, including molded onto the cover are pins which are designed in the form of coding pins and which engage in pin sockets on the spring element support when the cover is in its closed position.

10. The board-to-board connector of claim 1, wherein said signal-transmitting connection is in a magnetic resonance imaging scanner.

11. An assembly of a magnetic resonance imaging scanner, comprising a first printed circuit board and a second printed circuit board which are connected with one another in a signal-transmitting manner by means of a board-to-board connector, wherein the board-to-board connector has a main body with a first socket for a contact section of the first printed circuit board and a second socket for a contact section of the second printed circuit board, wherein a spring element support with a plurality of spring elements is provided between the first socket and the second socket, wherein each of the spring elements makes electrically conductive contact with a contact of the respective contact sections under spring-loaded contact pressure, such that the second socket is formed in part by a pivotable cover connected to the main body which can be moved between an open and a closed position, such that the second socket is formed by a guide molded onto the pivotable cover, and that the first socket is formed in part by the spring element support, such that the first socket is formed by a guide molded onto the spring element support.

* * * * *